United States Patent [19]

Krstenansky et al.

[11] Patent Number: 4,535,169

[45] Date of Patent: Aug. 13, 1985

[54] 5H-6-OXO-2,3,4,4A,7,7A-HEXAHY-DROPYRANO[2,3-B]PYRROLE AND THE PREPARATION THEREOF

[75] Inventors: John L. Krstenansky, Tucson, Ariz.; Bruce L. Currie, Woodridge, Ill.

[73] Assignee: The Board of Trustees of the University of Illinois, Urbana, Ill.

[21] Appl. No.: 530,992

[22] Filed: Sep. 12, 1983

[51] Int. Cl.$^3$ .......................................... C07D 471/04
[52] U.S. Cl. .................................... 548/453; 548/336; 260/112.5 R; 260/112.5 LH
[58] Field of Search .......................................... 548/453

Primary Examiner—Richard L. Raymond
Assistant Examiner—D. B. Springer
Attorney, Agent, or Firm—Marshall, O'Toole, Gerstein, Murray & Bicknell

[57] ABSTRACT

Conformationally restricted peptide analogs incorporating a rigid β-bend are formed by replacing a portion of the peptide backbone chain with a bicyclic heterocycle, 5H-6-oxo-2,3,4,4a,7,7a-hexahydropyrano[2,3-b]pyrrole. Properly substituted derivatives of the pyranopyrrole are conformationally rigid and cannot assume non-β-bend conformations in the interior of the peptide chain, while the terminal binding residues are maintained in the proper orientation for receptor interaction. Also described are a novel intermediate for preparation of the peptide analogs and a method for preparation of the intermediate.

2 Claims, No Drawings

5H-6-OXO-2,3,4,4A,7,7A-HEXAHYDROPYRANO[2,3-B]PYRROLE AND THE PREPARATION THEREOF

This invention relates to synthetic neuropeptide analogs in which a portion of the backbone chain has been replaced with a rigid heterocyclic structure that maintains a conformationally rigid β-bend in the molecule, to a novel intermediate compound useful in the preparation of such analogs, and to a method for the preparation of the intermediate compound.

BACKGROUND

A β-bend is a reversal in the direction of the backbone chain of a peptide, as a result of which the peptide becomes folded and more compact, and assumes a more stable conformation. Further, since the binding portions of the peptide are held in proper orientation for receptor interaction, a neuropeptide including a β-bend typically serves as a better ligand for a receptor site. Some neuropeptides, such as the cyclic peptides oxytocin, somatostatin and vasopressin, exist naturally in predominantly bent forms. Linear neuropeptides, which are flexible can assume a variety of conformations, including a β-bend, typically as a result of hydrogen bonding or solvent interaction. Such bonds are weak, however, and to the extent that they are destroyed, the biological activity of the peptide is diminished.

Previous attempts to introduce a conformational restriction in linear peptides involved replacing certain amino acid residues with other amino acids containing bulkier side chains, which limit the rotational space accessible about the backbone, and cyclizing the peptides, forcing them into a folded structure. These approaches share some undesirable characteristics. First, the introduction of the bulky groups of the added functionalities necessary to bend the peptide offer the possibility that these groups will interfere with the interaction with the receptor, even though they may promote the proper backbone conformation. Secondly, these analogs are far from rigid, and, even though their conformational space is somewhat restricted, these compounds can assume a variety of conformational states in addition to the desired β-bend.

An analog of methionine enkephalin incorporating an intermediate perhydronaphthalene moiety in the backbone chain for maintaining a permanent β-bend is known (Belanger et al., Can. J. Chem. 60, 1019–1029, 1982). The perhydronaphthalene derivative, however, was found to have only weak biological activity.

BRIEF DESCRIPTION OF THE INVENTION

In accordance with the present invention, a portion of the backbone chain of a linear peptide is replaced with a rigid bicyclic heterocycle of a particular configuration which introduces a permanent β-bend in the molecule, while maintaining three-dimensional relationships similar to those found in the natural β-bend. The terminal residues of the peptide, which directly interact with a receptor, are thus maintained in the proper three-dimensional orientation required for activity. Further, since a substantial portion of the original peptide linkages are eliminated in the analogs of the invention, the analogs become more resistant to enzymatic degradation, a potential defect of linear peptides.

The bicyclic heterocycle used in the present invention to create a permanent β-bend in a peptide chain is 2,3,4,4a,7,7a-hexahydro-6-oxo-5H-pyrano[2,3-b]pyrrole. This compound is known (Canonica et al., Gazz. Ital. Acta 87:998–1013 (1957); Audigier et al., Eur. J. Pharmacol. 63:35–46 (1980)), but no other compounds incorporating this ring system have been reported.

By attaching suitable amino acid residues or peptides to appropriate positions in the heterocycle, there can be obtained analogs of peptides having the terminal structures necessary for activity but wherein the interior of the chain is maintained in a permanent β-bend configuration by the bicyclic heterocycle.

The invention includes within its scope a novel intermediate compound which facilitates the preparation of the analog peptides of the invention, as well as a method of preparation of the intermediate.

DETAILED DESCRIPTION

In one aspect of the invention there are provided analogs of naturally occurring linear peptides which are modified in accordance with the invention to provide a permanent β-bend. Such analogs can be represented by the general formula

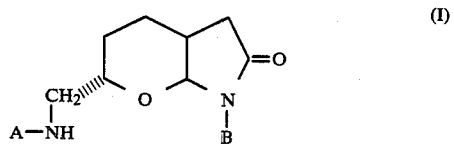

(I)

wherein A and B are the terminal portions of the natural peptide. A and B can each comprise hydrogen, an amino acid residue, or a peptide chain found in the natural peptide. Since the bicyclic heterocycle is in effect the equivalent of three amino acid residues, the sum of the amino acid residues in A and B is 3 less than the total number of amino acid residues in the natural peptide whose analog is made in accordance with the invention.

In another aspect of the invention, there are provided peptides incorporating a β-bend which are not necessarily directly analogous to any naturally occurring peptides. Such compounds can be represented by the general formula

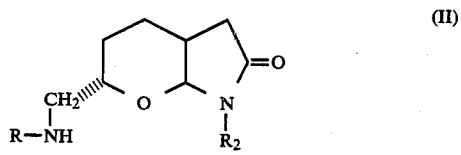

(II)

where $R_1$ is H, an amino acid residue, or a peptide attached through an amide linkage,

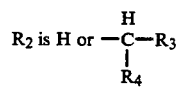

$R_3$ is H or a side chain found in a natural amino acid,

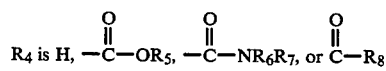

$R_5$ is H, methyl, ethyl, n-propyl, tert-butyl or benzyl, $R_6$ and $R_7$ are each H, a C1–C8 alkyl group or an arylalkyl group having up to 12 carbon atoms, and $R_8$ is an amino acid or peptide attached through an amino group by an amide linkage, provided that at least one of $R_1$ and $R_2$ includes at least one amino acid residue or peptide.

In formula II, $R_3$ can be a side chain found in a natural amino acid, i.e., the side chain R in an amino acid having the formula

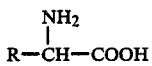

Accordingly, the side chain can be H (as in glycine), —CH$_3$ (as in alanine), —CH$_2$—CH—(CH$_3$)$_2$ (as in leucine), —CH$_2$OH (as in serine), benzyl (as in phenylalanine), and the like.

While the invention, in its broadest aspect, provides peptide analogs incorpating a permanent β-bend, without limitation as to the identity of the peptide, it is particularly applicable to analogs of the enkephalins and LHRH, which require β-bends for activity.

The enkephalins are pentapeptides which are the endogenous ligands for the opiate receptor. Leucine enkephalin ([Leu$^5$]-enkephalin) and methionine enkephalin ([Met$^5$]-enkephalin) share the initial tetrapeptide sequence Tyr-Gly-Gly-Phe-, differing only in the nature of the fifth residue as shown in the following formulas.

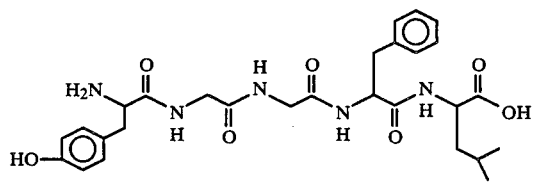

[Leu$^5$]-enkephalin

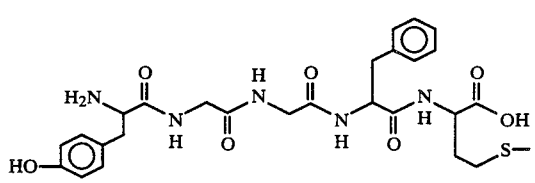

[Met$^5$]-enkephalin

Because of their chain-like structure, enkephalins are quite flexible and can assume a large number of conformations, among which is a β-bend created by hydrogen bonding between Leu$^5$ or Met$^5$ and Gly$^2$, known as a 5-2 β-bend. In accordance with the invention, the intermediate sequence -Gly-Gly-Phe- is replaced by the bicyclic heterocycle leaving the terminal portions free to interact with appropriate receptor sites. In the natural enkephalins, the terminal carboxyl in the fifth residue can be eliminated, esterified, converted to a primary or secondary amide, or coupled to other amino acids without substantial loss of activity (Beddel et al., Proc. Soc. Lond., Series B, 198:249–265, 1977).

Examples of enkephalin analogs in accordance with the invention include the following:

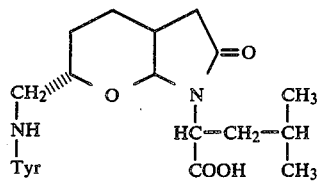
(1)

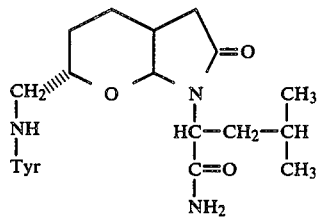
(2)

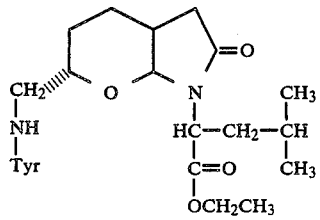
(3)

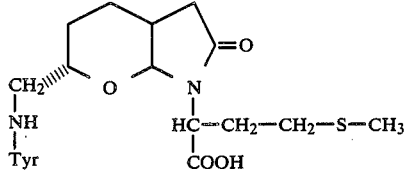
(4)

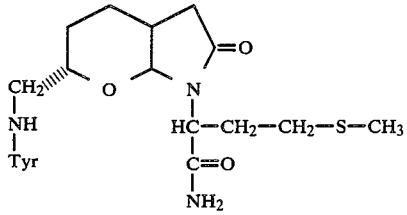
(5)

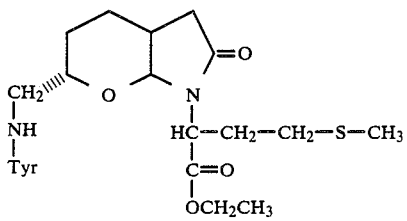
(6)

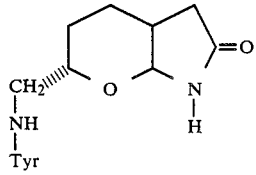
(7)

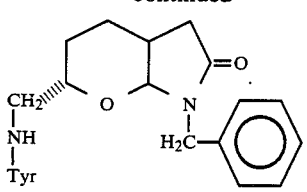

(8)

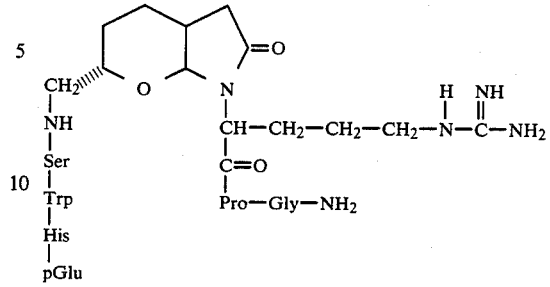

(10)

In the above list, compounds 1 and 4 correspond to Leu[5] enkephalin and Met[5] enkephalin, respectively, having a free carboxyl group. In the other compounds, the carboxyl group has been converted to an ester (compounds 3 and 6), an amide (compounds 2 and 5) or eliminated entirely (compounds 7 and 8). As in the case of the natural enkephalins, the compounds of the invention in which the terminal carboxyl group has been modified in this manner still exhibit biological activity.

The neuropeptide LHRH (luteinizing hormone-releasing hormone) is a decapeptide having the sequence pGlu-His-Trp-Ser-Tyr-Gly-Leu-Arg-Pro-Gly-NH$_2$, in which a β-bend centered about the Tyr[5] or Gly[6] residues appears to be necessary for biologic activity. In accordance with the invention, the sequence -Ser-Tyr-Gly- or -Tyr-Gly-Leu- is replaced by the bicyclic heterocycle used in the invention to produce LHRH analogs incorporating a permanent β-bend.

Examples of LHRH analogs in accordance with the invention include:

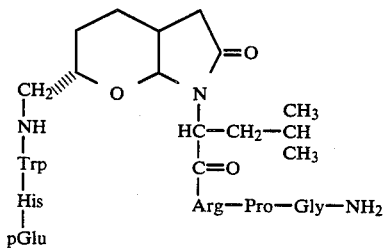

(9)

In compound 9, the heterocycle replaces the sequences -Ser-Tyr-Gly-, while in compound 10 it replaces the sequence -Tyr-Gly-Leu-.

The compounds of the invention can be made with the aid of a novel intermediate compound, (2S)-5H-2,3,4,4a,7,7a-hexahydro-6-oxo-2-(phthalimidomethyl)-pyrano[2,3-b]pyrrole having the structure

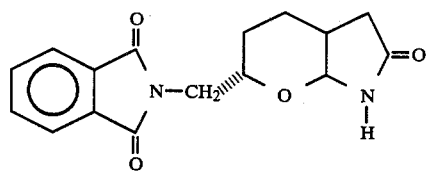

hereinafter referred to as "lactam C". Conformationally restricted analogs of the enkephalins are prepared by N-alkylating lactam C with an appropriate α-bromo ester, selectively removing the phthalimide blocking group by hydrazinolysis (Grundon et al., J. Chem. Soc. Perkin I, 1294–1295, (1980)) to yield the amine, which is then coupled to N-Boc-O-Bzl-tyrosine, or similar reagents containing other amino acid residues, (Pless et al. Helv. Chim. Acta, 62:398–411, (1979)), followed by removal of the blocking groups, as illustrated in the following procedure:

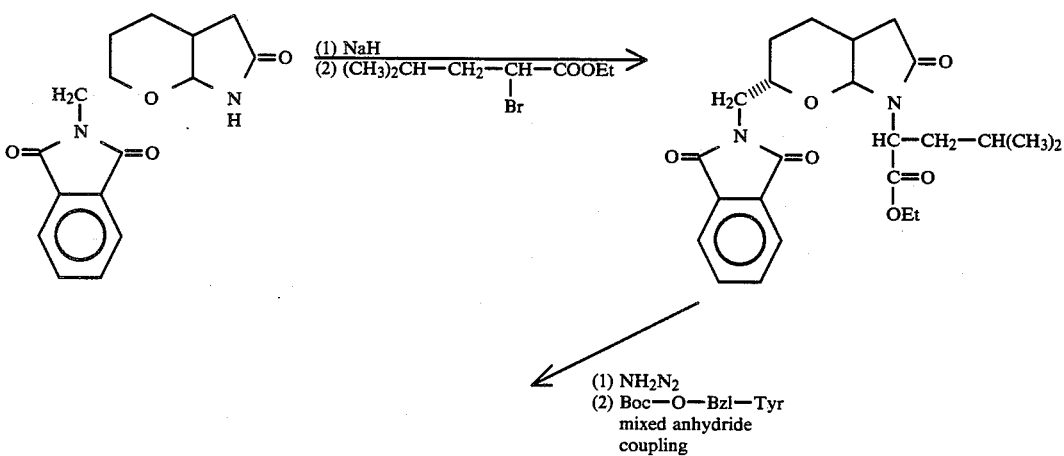

-continued

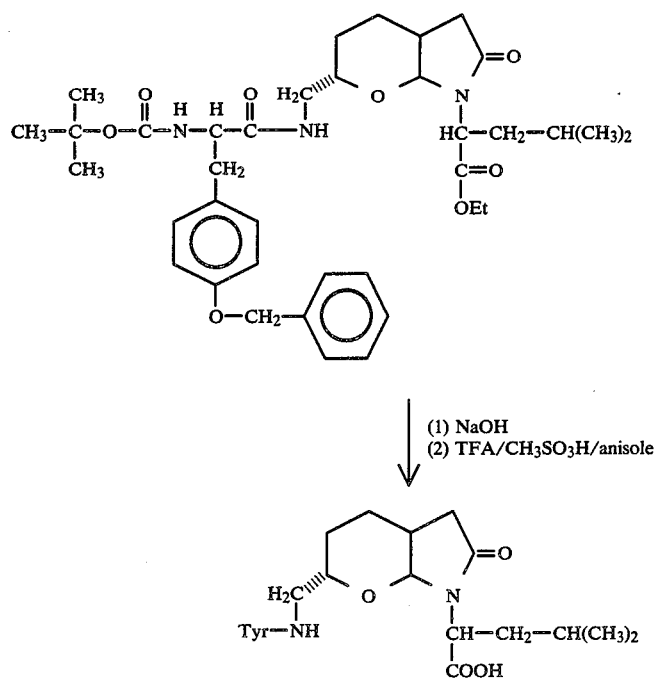

Analogs of LHRH can be made by N-alkylating lactam C, as described above, saponifying to obtain the free acid, coupling the Arg-(ω-Cbz$_2$)-Pro-Gly-NH$_2$ (Sheehan et al., J. Am. Chem. Soc., 71:1856–1861 (1949)), removing the phthalimide blocking group, coupling to pGlu-His-Trp-OH (Chang et al., J. Med. Chem., 15:623–627 (1972)), and removing the Cbz blocking groups by catalytic hydrogenation, as illustrated in the following procedure:

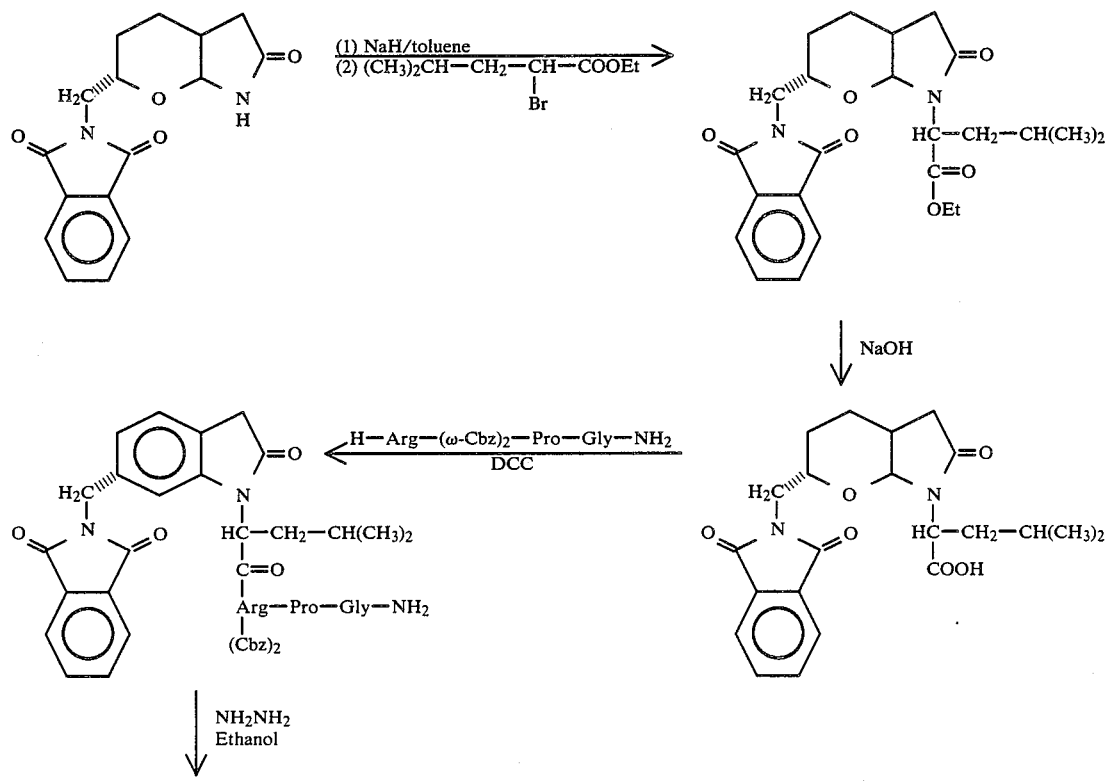

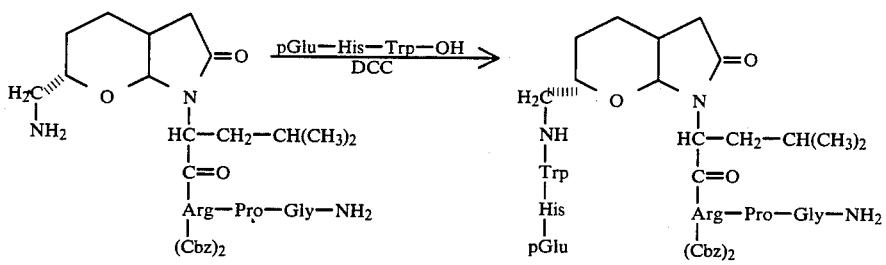

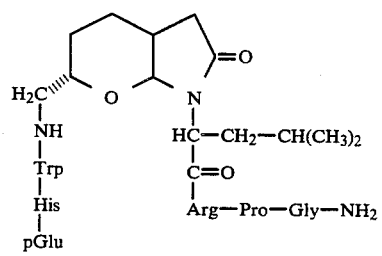

By suitable selection of the amino acid residues in the reactants, a variety of analogs of the enkephalins, LHRH, or other neuropeptides can be made.

Lactam C, the novel intermediate used as described above, is made by reducing 3,4-dihydro-2H-pyran-2-carboxamide to the amine, resolving the amine by fractional crystallization, e.g., as the (+)-tartrate salt, blocking the (+)-(2S)-amine as the (+)-(2S)-phthalimide derivative using N-carboethoxyphthalimide, cyclopropanating with lower alkyl (e.g., ethyl) diazoacetate and a catalyst (Hubert et al., Synthesis, 600–602 (1976); J. Org. Chem., 45:695–702 (1980)), hydrolyzing and recyclizing to the lactone, and treating with $NH_3$ to give the desired lactam, as shown in the following scheme:

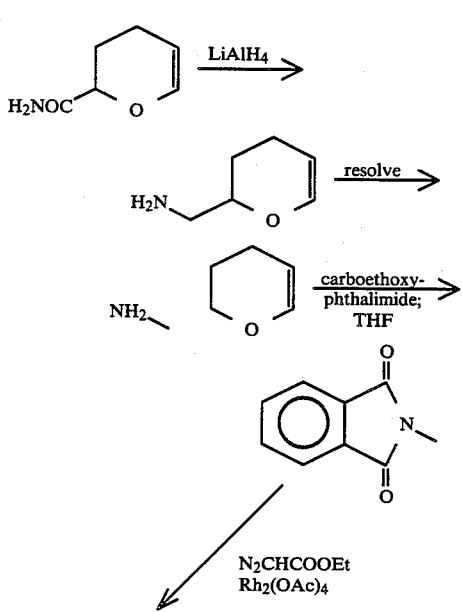

The preparation of typical embodiments of the invention is illustrated in the following examples.

EXAMPLE I (2S)-5H-2,3,4,4a,7,7a-Hexahydro-6-oxo-2-(phthalimidomethyl)pyrano[2,3-b]pyrrole (Lactam C)

A. 3,4-Dihydro-2H-pyran-2-methanamine

To an ice-bath cooled slurry of lithium aluminum hydride (25.0 g, 197 mmol) in anhydrous ether (500 mL) was added 3,4-dihydro-2H-pyran-2-carboxamide (25.0 g, 197 mmol) in portions. The flask was fitted with a condenser and drying tube and stirred at room temperature overnight. The mixture was again cooled using an ice-bath and water (25 mL) was slowly added through the top of the condenser. This was followed by the careful addition of 15% sodium hydroxide (25 mL) then water (75 mL). The mixture was stirred at room temperature for one hour then filtered. The white precipitate was washed with ether (300 mL). The combined ether filtrates were dried over anhydrous sodium sulfate and evaporated in vacuo leaving the crude amine as a colorless liquid.

B. (+)-(2S)-3,4-Dihydro-2H-pyran-2-methanamine tartrate

The amine was carefully added to a boiling solution of (+)-tartaric acid (29.6 g, 197 mmol) in anhydrous methanol (150 mL). The solution was allowed to stand overnight at room temperature. The partially resolved amine tartrate salt which crystallized from the methanolic solution was filtered, dried and repeatedly recrystallized from methanol until a constant optical rotation was obtained for the salt (approx. 6–10 recrystallizations). Yield 10.0 g (39%), m.p. 115°–118° C.; Anal. Calcd. for $C_{10}H_{17}NO_7 \cdot \frac{1}{2}H_2O$: C, 44.12; H, 6.66; N, 5.14. Found: C, 43.77; H, 6.61; N, 5.01.

C. (+)-(2S)-(Phthalimidomethyl)-3,4-dihydro-2H-pyran

The amine tartrate (107.0 g, 407 mmol) was added to 4N sodium hydroxide (310 mL) and extracted with ether (3×100 mL). The ether was dried over anhydrous sodium sulfate and evaporated in vacuo. The amine which remained was dissolved in tetrahydrofuran (450 mL). With stirring, N-carboethoxyphthalimide (89.60 g, 409 mmol) was added to the solution. The mixture was refluxed overnight then evaporated in vacuo. The residue was taken up into benzene (660 mL) and water (180 mL). The layers were separated and the organic layer was washed with water (180 mL), 5% sodium hydroxide (180 mL), water (2×180 mL), and saturated brine (180 mL). The organic layer was dried over anhydrous sodium sulfate and evaporated in vacuo leaving the crude product (97.0 g) as a white solid. This was recrystallized from ether-petroleum ether (1:1). Yield 72.64 g (73%), m.p. 87°–88° C.; Anal. Calcd. for $C_{14}H_{13}NO_3$: C, 69.12; H, 5.39; N, 5.76. Found: C, 69.18; H, 5.36; N, 5.66.

D. (6S)-2-Oxo-6-(phthalimidomethyl)-3a,5,6,7a-tetrahydro-4H-furo[2,3-b]pyran A solution of the product of the previous step (64.55 g, 266 mmol), rhodium (II) tetraacetate (1.53 g, 3.46 mmol), and anhydrous ether (275 mL) was stirred at room temperature for 20 minutes. Ethyl diazoacetate (39.93 g, 350 mmol) in ether (80 mL) was added dropwise over 18 hours. The reaction mixture was then run through a 60 mm dia.×60 mm alumina column followed by ether (500 mL). The combined ether eluant was evaporated leaving a golden oil. This was triturated with petroleum ether (5×50 mL). The golden oil that remained was crude cyclopropyl ester. The combined petroleum ether fractions were evaporated and the yellow liquid residue was placed atop a 60 mm dia.×60 mm alumina column and eluted with petroleum ether-ethyl acetate (9:1) (400 mL) followed by ethyl acetate (300 mL). The first 350 mL of eluant was discarded as this contained primarily the by-products of the reaction, diethyl maleate fumarate. The next 150 mL fraction was collected and evaporated in vacuo leaving crude cyclopropyl ester. This was combined with the other portion of crude cyclopropyl ester and dissolved in dioxane (150 mL) and 1N sulfuric acid (100 mL) then mechanically stirred and refluxed for three days. Then powdered barium hydroxide monohydrate (9.47 g, 50.0 mmol) was added to the solution, which was stirred for another hour. The mixture was filtered through Celite and the filtrate evaporated in vacuo. The brown residue was azeotroped with benzene (400 mL) for two days. The solution was evaporated in vacuo and the dark brown residue was eluted with chloroform through a 90 mm dia.×90 mm silica gel column. The eluant was evaporated in vacuo leaving 80.10 g of an orange oil. This was dissolved in anhydrous methanol (80 mL) and was allowed to stand at room temperature. The lactone, which crystallized, was filtered, washed with methanol and dried. Yield 21.94 g (28%), m.p. 186°–189° C.; Anal. Calcd. for $C_{16}H_{15}NO_5$: C, 63.78; H, 5.02; N, 4.65. Found: C, 63.62; H, 5.18; N, 4.57.

E. (2S)-5H-2,3,4,4a,7,7a-Hexahydro-6-oxo-2-(phthalimidomethyl)pyranol[2,3-b]pyrrole (Lactam C)

The lactone from the preceding step (21.5 g, 87.7 mmol) was placed in a pressure vessel with methanolic ammonia (stad. at 0° C.) (500 mL). The mixture was stirred at room temperature for one hour, then placed in an oil bath at 110° C. overnight. Upon cooling, the autoclave was opened and the methanolic ammonia evaporated in vacuo. The residue was eluted on a 60 mm dia.×50 mm silica gel column with chloroform (200 mL) followed by chloroform-acetone (1:1) (1000 mL). The eluant was evaporated in vacuo and the residue dissolved in chloroform-acetone (4 mL). Ether (100 mL) was added to the mixture and after three days 2.45 g of product was filtered from the solution. The careful addition of petroleum ether to the filtrate gave 3.10 g more product. Yield 5.65 g (26%) m.p. 229°–232° C.; Anal. Calcd. for $C_{16}H_{16}N_2O_4$: C, 63.99; H, 5.37; N, 9.33. Found: C, 63.72; H, 5.36; N, 9.43.

EXAMPLE 2

7-Substituted (2S)-5H-2,3,4,4a,7a-hexahydro-6-oxo-(tyrosylaminomethyl)pyrano[2,3-b]pyrroles

A. 7-Substituted (2S)-5H-2,3,4,4a,7,7a-hexahydro-6-oxo-2-(phthalimidomethyl)-pyranol]2,3-b]pyrroles

1. General Method

Lactam C was refluxed with a slurry of sodium hydride (2 equiv.) in dry toluene for two hours. Then a suitable alkyl bromide (2 equiv.) was added to the slurry and the mixture was refluxed overnight. The mixture was then filtered and the filtrate evaporated in vacuo. The residue was eluted through a 45 mm dia.×30 mm silica gel column using chloroform. The initial colorless eluant, which contained unreacted alkyl bromide, was discarded and the following 200 mL of yellow eluant was collected and evaporated in vacuo, leaving the crude product as a golden liquid. Diastereomers were separated by HPLC on a ¾ inch O.D.×3 foot methylphenyl reverse-phase preparative column. Acetonitrile-water (2:3) was the solvent utilized for the separation. The products were recovered from the fractions by first removing the acetonitrile in vacuo then extracting the aqueous mixture with ethyl acetate. The ethyl acetate was dried over anhydrous sodium sulfate and evaporated in vacuo, leaving the product.

2. 7-(1-carboethoxy-3-methylbutyl derivatives

Ethyl 2-bromo-4-methylpentanoate (2.45 g, 11 mmol), sodium hydride (264 mg, 11 mmol), and lactam C (1.60 g, 5.33 mmol) were used in the alkylation. Three major fractions were collected from the HPLC separation. Fraction 1 constituted the first major peak to elute from the column. Fraction 2 constituted the major portion of the second major peak to elute from the column. Fraction 3 constituted the tail end of this second major peak.

(a) Fraction 1

Yield 292 mg (12%) as a colorless oil, $[\alpha]_D^{27} +16.5$ (c 0.98, chloroform). Anal. Calcd. for $C_{24}H_{30}N_2O_6$: C, 65.14; H, 6.83; N, 6.33. Found: C, 63.10; H, 7.04; N, 5.42.

(b) Fraction 2

Yield 269 mg (11%) as a colorless oil, $[\alpha]_D^{27} -37.5$ (c 1.11, chloroform). Anal. Calcd. for $C_{24}H_{30}N_2O_6$: C, 65.14; H, 6.83; N, 6.33. Found: C, 62.14; H, 7.28; N, 4.70.

(c) Fraction 3

Yield 134.1 mg (6%) as a white crystalline solid, m.p 120°-121° C.; $[\alpha]_D^{27} -24.1$ (c 1.06, chloroform). Anal. Calcd. for $C_{24}H_{30}N_2O_6$: C, 65.14; H, 6.83; N, 6.33. Found: C, 65.04; H, 6.84; N. 6.27.

B. 7-Substituted (2S)-5H-2,3,4,4a,7,7a-hexahydro-6-oxo-2-(N-t-butoxycarbonyl-O-benzyltyrosylaminomethyl)pyrano[2,3-b]pyrroles

1. Method

The phthalimide blocking group was removed from the 7-substituted-hexahydro-6-oxo-2-(phthalimidomethyl)pyrano[2,3-b]-pyrroles by dissolving in anhydrous ethanol (5.0 mL) and adding 1M hydrazine hydrate in ethanol (1.1 equiv.) and stirring at room temperature overnight according to the method of Grundon et al. (J. Chem. Soc. Perkin I, 62: 398–411 (1979)). The ethanol was evaporated and the residue taken up into 2N hydrochloric acid (5.0 mL). The mixture was heated at 55° C. for 5 minutes and cooled to room temperature. The mixture was filtered and the filtrate was lyophilized to give the crude amine hydrochloride. N-Boc-O-benzyl-tyrosine (2.0 equiv.) and N-methylmorpholine (2.0 equiv.) were dissolved in ethyl acetate (2.0 mL). This mixture was stirred in an ice bath and isobutylchloroformate (2.0 equiv.) was added. After an eight minute activation period at 0° C., the amine hydrochloride (1.0 equiv.) in ethyl acetate (1.0 mL) with N-methylmorpholine (1.0 equiv.) was added and allowed to stir at 0° C. for two hours, then at room temperature overnight according to the method of Pless et al. (Helv. Chim. Acta, 62:398-411, (1979)). The mixture was then added to ethyl acetate (50 mL) and washed with water (2×20 mL), 1N hydrochloric acid (2×20 mL), 10% sodium bicarbonate (2×20 mL), and saturated aqueous sodium chloride (20 mL). The organic layer was dried over anhydrous sodium sulfate and evaporated in vacuo, leaving the crude blocked product. This was purified by preparative HPLC using a ¾ inch O.D.×3' long methylphenyl reverse-phase column and acetonitrile-water (1:1).

2. 7-(1-Carboethoxy-3-methylbutyl) derivative

(a) Fraction 1 Product

From 291.9 mg (0.660 mmol) of Fraction 1 of step A was obtained 82.2 mg (19%) product as a slightly yellowish oil that appeared as one spot by tlc (Rf=0.91 chloroform-acetone (1:1); visualized by UV and $Cl_2$/tolidine).

(b) Fraction 2 Product

From 268.7 mg (0.608 mmol) of Fraction 2 of Step A was obtained 107.4 mg (27%) product as a slightly yellowish oil that appeared as two spots by tlc (Rf=0.83 major, 0.90 minor; chloroform-acteone (1:1); visualized by UV and $Cl_2$/tolidine).

(c) Fraction 3 Product

From 247.6 mg (0.560 mmol) of Fraction 3 of step A was obtained 314.8 mg (84%) product as a slightly yellowish oil that appeared as one spot by tlc (Rf=0.89 chloroform-acetone (1:1); visualized by UV and $Cl_2$/tolidine).

C. 7-Substituted (2S)-5H-2,3,4,4a,7,7a-hexahydro-6-oxo-2-(tyrosylaminomethyl)pyrano[2,3-b]pyrroles

1. Method

Saponification of the ester was achieved by dissolving the ester in ethanol (2 mL) containing 1N sodium hydroxide (1 equiv.) and stirring for 4 hours. The mixture was evaporated in vacuo. The O-benzyl and N-t-butoxycarbonyl blocking groups were removed by stirring the compound at 0° C. with thioanisole (50 equiv.), methanesulfonic acid (70 equiv.), and trifluoroacetic acid (250 equiv.) for one hour. The mixture was evaporated in vacuo at 0° C. to remove the trifluoroacetic acid. The residue was added to water (2 mL) and washed with hexane (4×2 mL) to remove the thioanisole. The aqueous layer was made slightly basic with 5N sodium hydroxide then extracted with ethyl acetate (4×3 mL), dried over anhydrous sodium sulfate and evaporated in vacuo. The residue was dissolved in absolute ethanol (2 mL) and cooled to 0° C. Hydrogen chloride gas was then bubbled through the solution. The solution was evaporated in vacuo leaving the product as the hydrochloride salt. Final purification was carried out using preparative silica gel thin layer chromatography. (chloroform-methanol (4:1)).

2. 7-(1-Carboxy-3-methylbutyl) derivatives

(a) Fraction 1 Product

From 82.2 mg (0.124 mmol) of Fraction 1 of step B was obtained 1.3 mg (2%) of the final product as the hydrochloride salt. One spot by tlc (Rf=0.63 chloroform-methanol (4:1); visualized by ninhydrin, $Cl_2$/tolidine, and Pauly reagent).

(b) Fraction 2 Product

From 107.4 mg (0.162 mmol) of Fraction 2 of step B was obtained 1.8 mg (3%) of the final product as the hydrochloride salt. One spot by tlc (Rf=0.63 chloroform-methanol (4:1); visualized by ninhydrin, $Cl_2$/tolidine, and Pauly reagent).

(c) Fraction 3 Product

From 310.7 mg (0.467 mmol) of Fraction 3 of step B was obtained 2.0 mg (1%) of the final product as the hydrochloride salt. One spot by tlc (Rf=0.63 chloroform-methanol (4:1); visualized by ninhydrin, $Cl_2$/tolidine, and Pauly reagent).

EXAMPLE 3

LH-RH Analog (Compound 9)

Lactam C was heated with sodium hydride (2 equiv.) under reflux in toluene for 2 hours. Then ethyl 2-bromo-4-methylpentanoate (2 equiv.) was added to the slurry and the mixture was refluxed overnight. The product was purified by chromatography on silica gel using chloroform as the eluant. The ethyl ester was saponified by stirring the ester in ethanol containing 1 equiv. of 1N sodium hydroxide for 4 hours at room temperature. The mixture was evaporated and the residue after thorough drying in vacuo was coupled to Arg($\omega$-Cbz)$_2$-Pro-Gly-NH$_2$ using dicyclohexylcarbodiimide (Sheehan et al., J. Amer. Chem. Soc., 71:1856–1861 (1949)). The Arg($\omega$-Cbz)$_2$-Pro-Gly-NH$_2$ was obtained from Boc-Arg($\omega$-Cbz)$_2$-Pro-Gly-NH$_2$ after treating with trifluoroacetic acid to remove the Boc Group. The product obtained from the carbodiimide coupling was then treated with 1M hydrazine hydrate in ethanol (1.1 equiv.) to remove the phthalimide. After the usual workup, the amine was coupled to pGlu-His-Trp-OH (Chang et al., J. Med. Chem., 15:623–627 (1972)) using dicyclohexylcarbodiimide to effect the coupling. The Cbz blocking groups were then removed by catalytic hydrogenation over 10% palladium on charcoal to give the title compound.

The conformationally restricted peptide analogs of the invention have the same utility as the corresponding natural peptides. Thus, for example, the analogs of the enkephalins have analgesic properties, while the analogs of LHRH have luteinizing hormone releasing activity.

The foregoing detailed description has been given for clearness of understanding only, and no unnecessary limitations should be understood therefrom as modifications will be obvious to those skilled in the art.

What is claimed is:

1. A compound having the structure

2. The method of preparing the compound of claim 1 comprising the following steps:

(a) reducing a compound of the formula (I)

to produce a compound of the formula (II)

(b) resolving compound II as the tartrate salt and recovering the isomer having the formula (III)

(c) reacting compound III with N-carboethoxyphthalimide to produce a compound of the formula (IV)

(d) cyclopropanating compound IV to produce a compound of the formula (V)

where R is a $C_1$-$C_8$ alkyl, (e) hydrolyzing and recyclizing compound V by dehydration to produce a compound of the formula (VI)

(f) and reacting compound VI with ammonia under pressure to produce a compound of the formula (VII)

* * * * *

UNITED STATES PATENT AND TRADEMARK OFFICE
CERTIFICATE OF CORRECTION

PATENT NO. : 4,535,169
DATED : August 13, 1985
INVENTOR(S) : Krstenansky, et al.

It is certified that error appears in the above-identified patent and that said Letters Patent is hereby corrected as shown below:

Col. 2, the formula between lines 45 and 53 should read as follows:

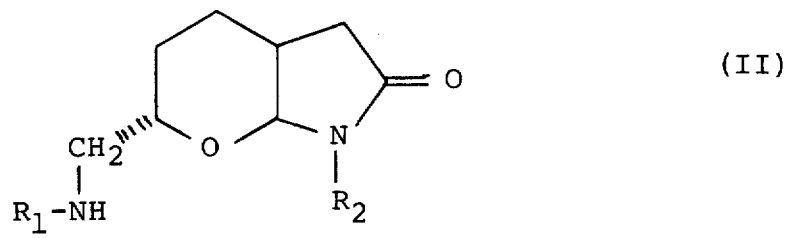

(II)

UNITED STATES PATENT AND TRADEMARK OFFICE
CERTIFICATE OF CORRECTION

PATENT NO. : 4,535,169
DATED : August 13, 1985
INVENTOR(S) : Krstenansky, et al.

It is certified that error appears in the above-identified patent and that said Letters Patent is hereby corrected as shown below:

Col. 5, bottom left-hand corner, the formula should read as follows:

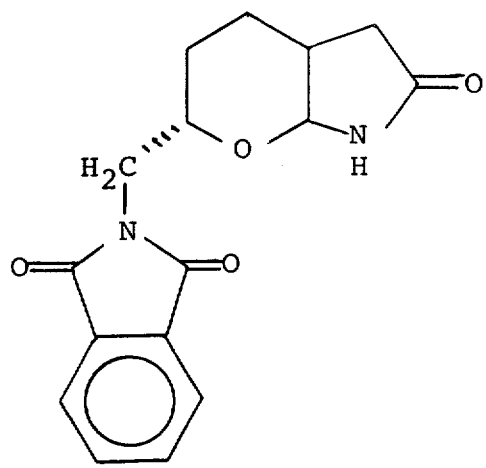

Col. 6, fourth line from the bottom, "(1) $NH_2N_2$" should read -- (1) $NH_2NH_2$ --

UNITED STATES PATENT AND TRADEMARK OFFICE
CERTIFICATE OF CORRECTION

PATENT NO. : 4,535,169   Page 3 of 8
DATED      : August 13, 1985
INVENTOR(S): Krstenansky, et al.

It is certified that error appears in the above-identified patent and that said Letters Patent is hereby corrected as shown below:

Col. 7, bottom left-hand corner, the formula should read as follows:

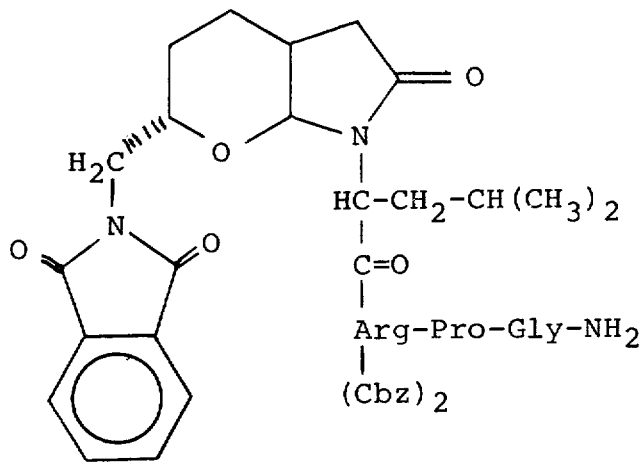

UNITED STATES PATENT AND TRADEMARK OFFICE
CERTIFICATE OF CORRECTION

PATENT NO. : 4,535,169  
DATED : August 13, 1985  
INVENTOR(S) : Krstenansky, et al.

Page 4 of 8

It is certified that error appears in the above-identified patent and that said Letters Patent is hereby corrected as shown below:

Col. 9, lines 55 to 69, the reaction should read as follows:

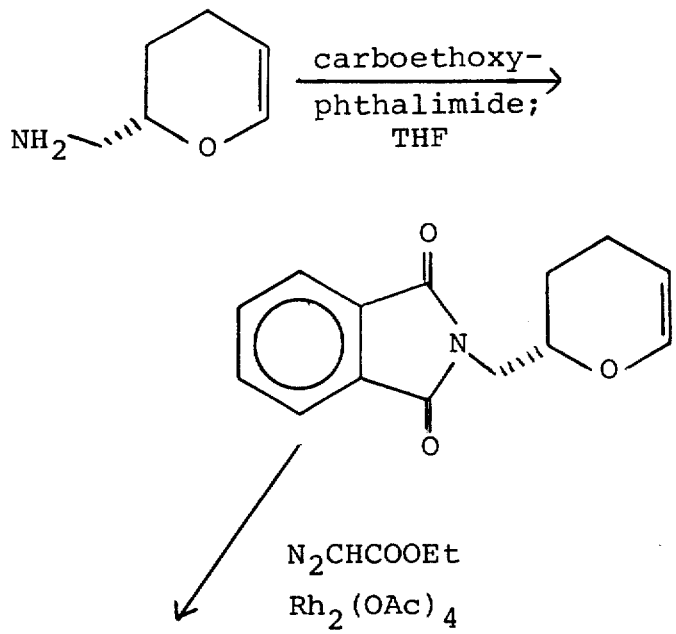

UNITED STATES PATENT AND TRADEMARK OFFICE
CERTIFICATE OF CORRECTION

PATENT NO. : 4,535,169  
DATED : August 13, 1985  
INVENTOR(S) : Krstenansky, et al.

It is certified that error appears in the above-identified patent and that said Letters Patent is hereby corrected as shown below:

The formula at the top of Col. 10 should read as follows:

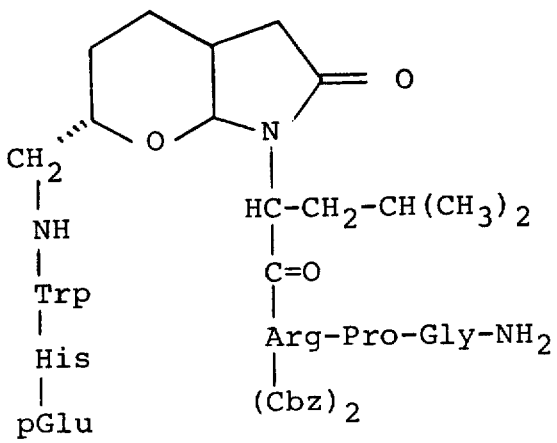

UNITED STATES PATENT AND TRADEMARK OFFICE
CERTIFICATE OF CORRECTION

PATENT NO. : 4,535,169

DATED : August 13, 1985

INVENTOR(S) : Krstenansky, et al.

It is certified that error appears in the above-identified patent and that said Letters Patent is hereby corrected as shown below:

Col. 10, between lines 30 and 50, each occurrence of "Pht" should be connected to the heterocyclic ring as follows:

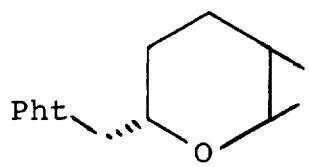

Col. 11, line 62, after "maleate", insert --and diethyl--.

Col. 12, line 19 should read as follows:
--(phthalimidomethyl)pyrano[2,3-b]pyrrole (Lactam C)--

Col. 12, line 22, "(stad. at 0°C.)" should read --(satd. at 0°C.)--

UNITED STATES PATENT AND TRADEMARK OFFICE
CERTIFICATE OF CORRECTION

PATENT NO. : 4,535,169

DATED : August 13, 1985

INVENTOR(S) : Krstenansky, et al.

It is certified that error appears in the above-identified patent and that said Letters Patent is hereby corrected as shown below:

Col. 12, line 46 should read as follows:
--(phthalimidomethyl)-pyrano[2,3-b]pyrroles--

Col. 12, line 61, "3/4 inch" should read --3/8 inch--.

Col. 13, line 66, "3/4 inch" should read --3/8 inch--.

Col. 14, line 15, "chloroform-acteone" should read --chloroform-acetone--.

UNITED STATES PATENT AND TRADEMARK OFFICE
CERTIFICATE OF CORRECTION

PATENT NO. : 4,535,169

DATED : August 13, 1985

INVENTOR(S) : Krstenansky, et al.

It is certified that error appears in the above-identified patent and that said Letters Patent is hereby corrected as shown below:

Col. 16, the formula at lines 16 to 23 should read as follows:

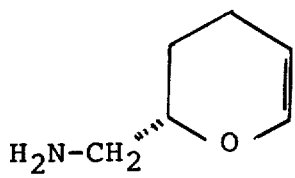

Signed and Sealed this

Third Day of June 1986

[SEAL]

Attest:

DONALD J. QUIGG

Attesting Officer

Commissioner of Patents and Trademarks